United States Patent [19]

Kawada et al.

[11] 4,066,760

[45] Jan. 3, 1978

[54] AGRICULTURAL AND HORTICULTURAL FUNGICIDAL COMPOSITIONS

[75] Inventors: Seigo Kawada, Fujieda; Shigeru Hayashi, Shizuoka, both of Japan

[73] Assignee: Kumiai Chemical Industries Ltd., Tokyo, Japan

[21] Appl. No.: 781,042

[22] Filed: Mar. 24, 1977

[30] Foreign Application Priority Data

Mar. 29, 1976 Japan .................................. 51-35013
Mar. 29, 1976 Japan .................................. 51-35014

[51] Int. Cl.$^2$ ........................ A01N 9/02; A01N 9/12; A01N 9/22
[52] U.S. Cl. .................................. 424/245; 424/274; 424/286
[58] Field of Search ......................... 424/245, 274, 286

[56] References Cited

U.S. PATENT DOCUMENTS

| | | | |
|---|---|---|---|
| 2,457,674 | 12/1948 | Heuberger | 424/286 X |
| 2,504,404 | 4/1950 | Flenner | 424/286 |
| 2,553,770 | 5/1951 | Kittleson | 424/134 X |
| 2,553,771 | 5/1951 | Kittleson | 260/313 |
| 2,553,776 | 5/1951 | Kittleson | 425/311 X |
| 2,710,822 | 6/1955 | Golding et al. | 424/286 |
| 3,050,439 | 8/1962 | Nemec et al. | 424/366 X |
| 3,379,610 | 4/1968 | Lyon et al. | 424/286 |
| 3,734,927 | 5/1973 | Kawada et al. | 424/274 X |
| 3,821,395 | 6/1974 | Kawada et al. | 424/274 |

OTHER PUBLICATIONS

Frear, Pesticide Index, 4th Ed., pp. 121 & 122 (1969).

*Primary Examiner*—Allen J. Robinson
*Attorney, Agent, or Firm*—Oblon, Fisher, Spivak, McClelland & Maier

[57] ABSTRACT

A fungicidal composition for agricultural and horticultural use comprising a suitable carrier and fungicidally effective amount of N-(4-fluorophenyl)-2,3-dichloromaleimide per part of at least 1 compound selected from the group consisting of a compound expressed by the formula:

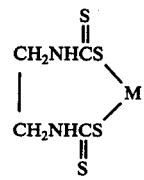

(where M represents manganese or zinc, and when M is manganese, zinc may coordinate in the molecules), N-trichloromethylthio-4-cyclohexene-1,2-dicarboxyimide and 8-oxyquinoline copper. The composition has been found to possess unusually high anti-fungal activity in protecting against various plant disease.

7 Claims, No Drawings

AGRICULTURAL AND HORTICULTURAL FUNGICIDAL COMPOSITIONS

BACKGROUND OF THE INVENTION

1. Field of the Invention

This invention relates to agricultural and horticultural fungicidal compositions, and more particularly to such fungicidal compositions containing at least one kind of known fungicidal compounds and N-(4-fluro-phenyl)-2,3-dichloromaleimide.

2. Description of the Prior Arts

One of the most serious problems that is encountered in culture of agricultural products is diseases. Various kinds of compounds such as organic metal compounds, chlorine compounds, antibiotics, etc., have been proposed and practically used as preventive agents against such disease. Neverthless, any of these compounds involves many problems in respect of antimicrobial spectrum, efficacy, toxicity, retention, damage from use of compounds and other matters, and some of these compounds have been condemned as more harmful than beneficial. Thus, strong request is voiced for development of a fungicide which is free of these problems.

Among the commercially available fungicides, the metal-containing ethylenebisdithiocarbamate compounds present an antimicrobial spectrum that shows high effect against gummy stem blight, anthracnose, alternaria leaf spot, melanose, ripe rot and other similar kinds of diseases which attack such plants as cucumber, tomato, melon, citrus fruits, apple, persimmons and grapes, but these compounds are poor in effect against scab and black rot of citrus fruits and gray leaf spot of tomato. On the other hand, N-trichloromethylthio-4-cyclohexene-1,2-dicarboxyimide or 8-oxyquinoline copper presents an antimicrobial spectrum demonstrating strong efficacy against anthracnose, leaf mold, scab, black spot and ripe rot which develop on cucumber, tomato, melon, apple, pear, grape and other like fruit trees, but such compounds are poorly protective against alternaria leaf spot of applies and melanose of citrus fruits. Also, some of these compounds could produce bad damage to the crops. N-(4-fluorophenyl)-2,3-dichloromaleimide also presents a wide antimicrobial spectrum indicating high efficacy for a variety of plant diseases such as anthracnose, apple scab, citrus scab, etc., but this compound is weak in effect against downy mildew of cucumber and gray leaf spot of tomato, and it is impossible to prevent such diseases with a normal concentration (750 - 1,500 ppm). It needs to use the compound at a concentration of over about 1,500 ppm for obtaining a satisfactory effect against these diseases, but such high concentration could cause serious damage to the new leaves. Thus, in use of such compound, minute care is required in determining the time of use and concentration of the compound.

The present inventors found that a suitable combination of these per se defective compounds could produce a surprisingly high effect against melanose of citrus fruits, downy mildew of cucumber, gray leaf spot of tomato and mildew of apple which can hardly be controlled perfectly by single use of these compounds, and that such combination could bring about an excellent effect with a far lower concentration that the normal use level required in single use of said compounds. Thus, the fungicidal compositions provided according to this invention are capable of controlling almost all kinds of diseases that plague the agricultural and horticultural plants. These compositions are also worth notice in that they can greatly expand the scope of use of the fungicidal compounds and that the required concentration of the active compounds in practical use can be reduced by suitable blending of these compounds.

SUMMARY OF THE INVENTION

The primary object of this invention, therefore, is to provide novel agricultural and horticultural fungicidal compositions which are safe in use and find a wide scope of application. Another object of this invention is to prevent various kinds of diseases on fruits, vegetables and other plants by using the novel agricultural chemical compositions according to this invention.

These objects can be accomplished by an agricultural and horticultural fungicidal composition which contains, as active ingredients, N-(4-fluorophenyl)-2,3-dichloromaleimide and at least one of the compounds selected from the group B consisting of compounds expressed by the following general formula:

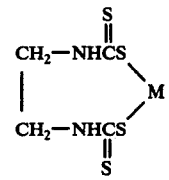

(where M represents manganese or zinc, and when M is manganese, zinc may coordinate in the molecules), N-trichloromethylthio-4-cyclohexene-1,2-dicarboxyimide and 8-oxyquinoline copper, according to the process of this invention.

DETAILED DESCRIPTION OF THE INVENTION

Shown in the following are the chemical structural formulae and physical properties of N-trichloromethylthio-4-cyclohexene-1,2-dicarboxyimide, 8-oxyquinoline copper, some examples of metal-containing ethylenebisdithiocarbamate compounds and N-(4-fluorophenyl)-2,3-dichloromaleimide which are used in preparation of the fungicidal compositions according to this invention. The compound numbers given below will be referred to in the ensuing description of the invention. Compound of Group B Compound B-1 N-trichloromethylthio-4-cyclohexene-1,2-dicarboxyimide

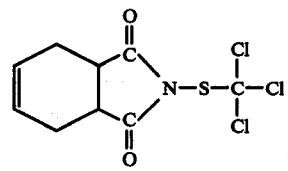

White powdery crystals; m.p.: 178° C

Compound B-2 8-oxyquinoline copper

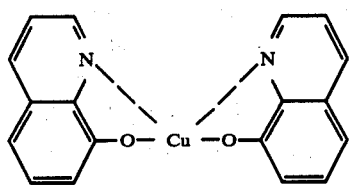

Yellow powdery crystals; m.p.: over 200° C (decomposed)

Compound B-3 Manganese ethylenebisdithiocarbamate

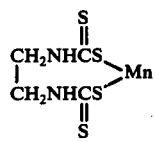

Yellow powdery crystals (decomposed before melting)

Compound B-4 Zinc ethylenebisdithiocarbamate

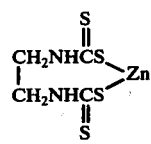

White powdery crystals (decomposed before melting)

Compound B-5 Zinc ion coordinated manganese ethylenebisdithiocarbamate

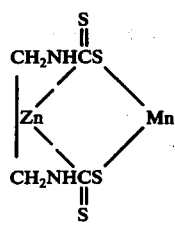

Yellow powdery crystals
Compound A N-(4-fluorophenyl)-2,3-dichloromaleimide

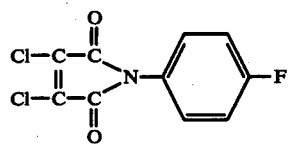

Yellow powdery crystals; m.p.: 245° – 246° C

The above-shown compounds B-1 to B-5 and A are all known kinds of compounds which may be prepared, for example, in the following ways.

Compound B-1 is disclosed in U.S. Pat. Nos. 2,553,770, 2,553,771 and 2,553,776 and can be produced from the following reaction:

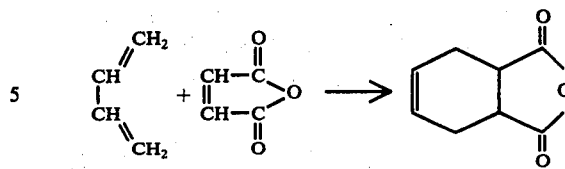

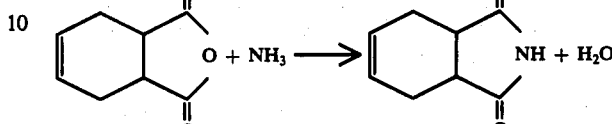

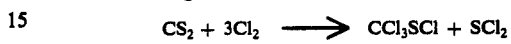

$$CS_2 + 3Cl_2 \longrightarrow CCl_3SCl + SCl_2$$

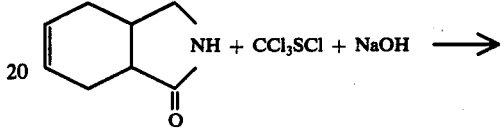

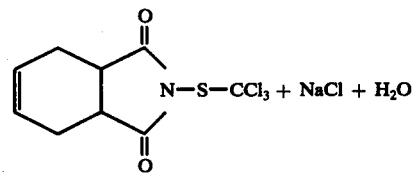

Compound B-2 is revealed in Pesticide Manual, 1974, issued by the British Crop Protection Council and can be produced from the following reaction:

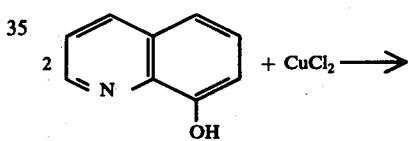

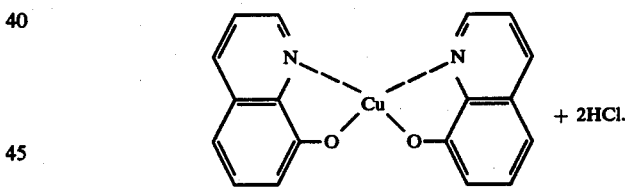

Compound B-3 is disclosed in U.S. Pat. No. 2,504,404 and 2,710,822 and can be prepared from the following reactions:

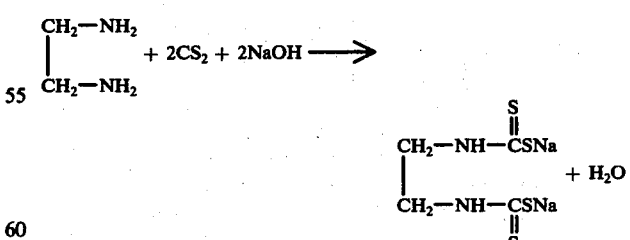

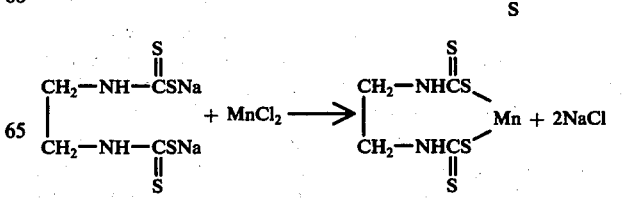

Compound B-4 is revealed in U.S. Pat. Nos. 2,457,674 and 3,050,439 and can be produced from the following reactions:

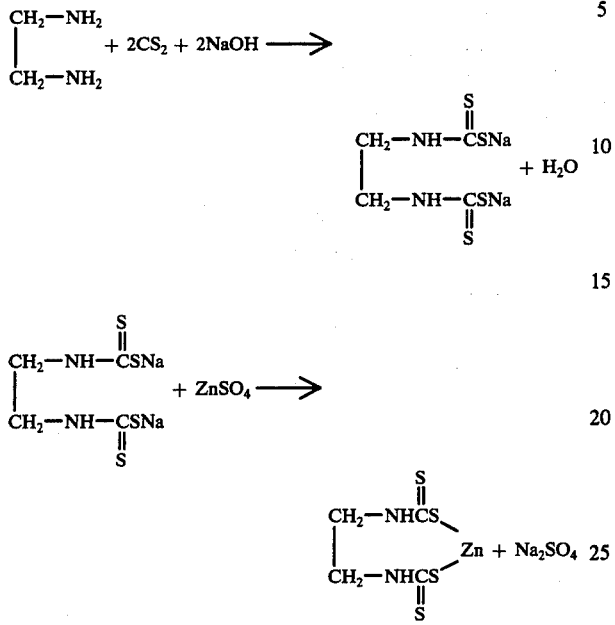

Compound B-5 can be produced by adding a zinc sulfate hydrate to Compound B-3 as described in U.S. Pat. No. 3,379,610.

Compound A is disclosed in U.S. Pat. Nos. 3,821,395 and 3,734,927 and can be prepared from the following reaction:

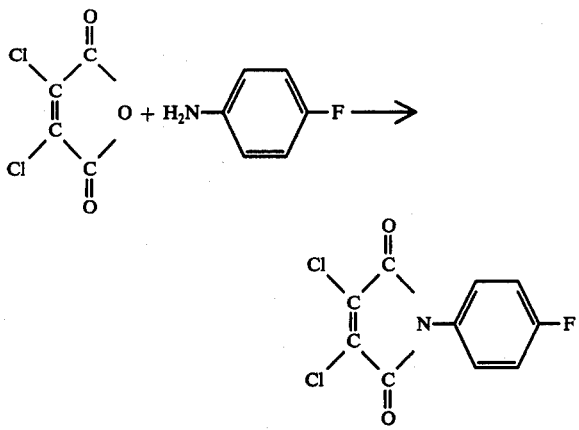

The agricultural and horticultural fungicidal compositions according to this invention are obtained by blending at least one of said Compounds B-1 to B-5 with Compound A, but actually they are further added with various kinds of adjuvants or diluents and prepared into various forms such as wettable powders, dust, granule, micro granules, etc., and these preparations may be immediately put to use or may be suspended in water or other aqueous medium for spray or spreading.

The diluent or assistants used in the compositions of this invention may be of the type generally employed in preparation of agricultural chemicals, such as for example talc, kaolin, clay, bentonite, diatom earth, water, DMF, DMSO, cyclohexane, toluene, xylene, petroleum solvents, alcohols, 2-ethoxyethanol, alkylbenzene sulfonates, polyoxyethylene alkylarylether, polyoxyethylene fatty acid ester, polyoxyethylene sorbitan monolaurate and lignin sulfonates.

The blending ratio of compounds of group B to Compound A in the fungicidal compositions according to this invention is 1:0.5, preferably 1:1, to 2 by weight. As for the use concentration of the fungicidal compositions of this invention, the desired object can be attained by using a composition containing as active ingredients, 20 to 200 ppm of Compound of group B and 100 to 500 ppm of Compound A, in the case of wettable powder. The compositions of this invention may be also blended with the active components of other types of agricultural chemicals such as insecticides or herbicides. For instance, mixing of such insectisides as dimethyldichlorovinyl phosphate, 0,0-dimethyl 0-(4-nitro-3-methylphenyl) thiophosphate, 1,1-bis(p-chlorophenyl)-2,2,2-trichloroethanol is recommendable for use intended to exterminate cutworms, aphids, scales or mites.

Now the preparations from the agricultural and horticultural fungicidal compositions of this invention and the fungicidal tests conducted on these compositions are described in detail by way of examples. It is to be however understood that the compounds, additives and their blending ratios usable in the present invention are not limited to those shown in the following examples but span a wider scope of variations. Percent (%) used in the following examples is by weight.

EXAMPLE 1

Dust

1% of Compound B-3, 2% of Compound A and 97% of diatom earth are uniformly mixed and pulverized into a dust. This dust may be immediately put to use by way of dusting or scattering.

EXAMPLE 2

Dust

2% of Compound B-2, 2% of Compound A and 96.0% of diatom earth are uniformly mixed and pulverized into a dust. This dust may be immediately used by way of spreading or scattering.

EXAMPLE 3

Wettable Powder

10% of Compound B-1, 20% of Compound A, 65% of fine silica powder, 3% of sodium dinaphthylmethanedisulfonate and 2% of sodium ligninsulfonate are uniformly mixed and pulverized into a wettable powder. For use of this wettable powder, it is diluted with water to a suitable concentration and then sprayed.

EXAMPLE 4

Wettable Powder

15% of Compound B-2, 25% of Compound A, 55% of diatom earth, 3% of sodium alkylbenzenesulfonate and 2% of sodium ligninsulfonate are uniformly mixed and pulverized into a wettable powder. This powder, when put to use, is diluted with water to a predetermined concentration and then sprayed.

EXAMPLE 5

Wettable Powder

15% of Compound B-4, 15% of Compound A, 65% of diatom earth, 3% of sodium alkylbenzenesulfonate and 2% of sodium ligninsulfonate are uniformly mixed and pulverized into a wettable powder. For use, it is diluted with water to a suitable concentration and then sprayed.

EXAMPLE 6

Wettable Powder

10% of Compound B-5, 20% of Compound A, 65% of fine silica powder, 3% of sodium dinaphthylmethanedisulfonate and 2% of sodium ligninsulfonate are uniformly mixed and pulverized to prepare a wettable powder. It is used after diluting it with water to a suitable concentration.

EXAMPLE 7

Granules

2% of Compound B-1, 4% of Compound A, 46% of bentonite, 46.5% of clay, 1% of sodium alkylbenzenesulfonate and 0.5% of polyvinyl alcohol are uniformly mixed and pulverized, then the mixture is further added with water and kneaded, and then formed into granules by an extrusion type granulator. These particles are then dried. For use, they may be spread or scattered in the form as they are.

EXAMPLE 8

Granules

2% of Compound B-4, 4% of Compound A, 48% of bentonite, 44.5% of clay, 1% of sodium alkylbenzenesulfonate and 0.5% of polyvinyl alcohol are uniformly mixed and pulverized, and the mixture is added with water and kneaded and then formed into granules by an extrusion type granulator, followed by drying. These granules may be immediately put to use by way of spreading or scattering.

Described in the following are the results of some tests conducted on the compositions of this invention.

TEST EXAMPLE 1

Effect on gray leaf spot of tomato (1)

The wettable powder prepared according to Examples 4 to 6 described above were diluted with water to a predetermined concentration, and these dilute solutions were sprayed at the rate of 300 ml per plant, to the tomato plant (var. ponderose) of the 6- to 7-leaf stage cultured in a vinyl chamber, with 5 tomato plants being planted in each plot, and thereafter each solution was applied three times at one-week intervals, thus applying each solution four times in all each solution was tested in three replicates. Appraisal was made one week after final application by counting the number of lesions per leaf on the 10 leaves positioned in succession upwardly of the third true leaf from the bottom and determining the protective value from the following formula:

Protective value (%) =

$$\frac{\text{nr. of lesion in control plant} - \text{nr. of lesions in treated plant}}{\text{nr. of lesions in control plant}} \times 100$$

Table 1

| Compounds tested | Concentration (ppm) | Nr. of lesion | Protective value | Phytotoxicity |
|---|---|---|---|---|
| Compound B-1 | 300 | 184.3 | 37.8 | None |
| Compound B-2 | 300 | 192.1 | 35.2 | None |
| Compound A | 750 | 158.4 | 46.6 | None |

Table 1-continued

| Compounds tested | Concentration (ppm) | Nr. of lesion | Protective value | Phytotoxicity |
|---|---|---|---|---|
| Compositions of this invention | | | | |
| Compound B-1 | 150 + 150 | 3.8 | 98.7 | None |
|  | 150 + 250 | 2.9 | 99.2 | None |
| + Compound A | 150 + 300 | 0.9 | 99.8 | None |
| Compound B-2 | 150 + 150 | 4.8 | 98.4 | None |
|  | 150 + 250 | 2.9 | 99.2 | None |
| + Compound A | 150 + 300 | 0.0 | 100.0 | None |
| Non-treated | — | 296.5 | 0 | None |

TEST EXAMPLE 2

Effect on gray leaf spot of tomato (2)

The tests were carried out in the similar manner as Test Example 1 by using the compounds shown in Table 2.

The results are shown below.

Table 2

| Compound tested | Concentration (ppm) | Nr. of lesions | Protective value | Phytotoxicity |
|---|---|---|---|---|
| Compound B-3 | 300 | 163.2 | 41.2 | None |
| Compound B-4 | 300 | 175.1 | 36.9 | None |
| Compound B-5 | 300 | 186.5 | 32.8 | None |
| Compound A | 750 | 181.2 | 38.3 | None |
| Compositions of this invention | | | | |
| Compound B-3 | 150 + 150 | 1.0 | 99.6 | None |
|  | 150 + 250 | 0.0 | 100.0 | None |
| + Compound A | 150 + 300 | 0.0 | 100.0 | None |
| Compound B-4 | 150 + 150 | 4.7 | 98.3 | None |
|  | 150 + 250 | 3.1 | 98.8 | None |
| + Compound A | 150 + 300 | 0.0 | 100.0 | None |
| Compound B-5 | 150 + 150 | 6.2 | 97.8 | None |
|  | 150 + 250 | 4.0 | 98.5 | None |
| + Compound A | 150 + 300 | 0.0 | 100.0 | None |
| Non-treated | — | 277.5 | 0 | None |

TEST EXAMPLE 3

Effect on downy mildew of cucumber (1)

The wettable powder prepared according to Examples 4 to 6 were diluted with water to a predetermined concentration and these dilute solutions were sprayed at the rate of 30 ml per pot to the pot-cultured cucumbers (var. sagami hanjiro) of the bifoliate stage, and the next day, a suspension of conidia (10 to 15 pieces in one view field (10 × 15) of the microscope) of pseudo perono spore cubemsis ROSTOWZEW collected from the infected cucumbers was inoculated by spraying, and the thus treated cucumbers were placed in a humid vinyl chamber for three days and then transferred into a green house to allow growth of the mildew lesions. 10 days after inoculation, the healthy leaves and infected leaves of the cucumbers were examined. The results are shown in Table 3.

Table 3

| Compounds tested | Concentration (ppm) | Nr. of healthy leaves | Nr. of infected leaves | Percent of infected leaves |
|---|---|---|---|---|
| Compound B-1 | 300 | 3 | 47 | 94.0 |
| Compound B-2 | 300 | 0 | 49 | 100.0 |
| Compound A | 750 | 6 | 40 | 87.0 |
| Compositions of this invention | | | | |
| Compound B-1 | 150 + 150 | 48 | 4 | 7.7 |
|  | 150 + 250 | 48 | 2 | 4.0 |
| + Compound A | 150 + 300 | 47 | 0 | 0.0 |
| Compound B-2 | 150 + 150 | 48 | 5 | 9.4 |
|  | 150 + 250 | 47 | 2 | 4.0 |
| + Compound A | 150 + 300 | 47 | 1 | 2.0 |
| Non-treated | — | 0 | 49 | 100 |

TEST EXAMPLE 4

Effect on downy mildew of cucumber (2)

The tests were carried out in the similar manner as Test Example 3 by using the compounds shown in Table 4.

Table 4

| Compound Tested | Concentration (ppm) | Nr. of healthy leaves | Nr. of infected leaves | Percent of infected leaves |
|---|---|---|---|---|
| Compound B-3 | 300 | 2 | 46 | 95.8 |
| Compound B-4 | 300 | 2 | 49 | 96.1 |
| Compound B-5 | 300 | 3 | 49 | 94.2 |
| Compound A | 750 | 6 | 40 | 87.0 |
| Compositions of this invention | | | | |
| Compound B-3 | 150+150 | 53 | 2 | 3.6 |
|  | 150+250 | 51 | 1 | 1.9 |
| + Compound A | 150+300 | 48 | 0 | 0.0 |
| Compound B-4 | 150+150 | 47 | 4 | 8.0 |
|  | 150+250 | 49 | 3 | 5.7 |
| + Compound A | 150+300 | 47 | 1 | 2.1 |
| Compound B-5 | 150+150 | 49 | 1 | 2.0 |
|  | 150+250 | 48 | 0 | 0.0 |
| + Compound A | 150+300 | 52 | 0 | 0.0 |
| Non-treated | — | 0 | 49 | 100.0 |

TEST EXAMPLE 5

Preventive effect on melanose of citrus fruits

The wettable powder prepared according to the Example 5 were diluted with water to a predetermined concentration and these solutions were applied at the rate to 600 l/10a to the potted citrus fruit seedlings (var. mandarin orange) immediately after development of new leaves, and two days later, a suspension of spores of diaporthe citri wolf cultured on citrus plant was inoculated by spraying.

After inoculation, the treated seedlings were kept in a humid vinyl chamber at 25° C for 2 days and then transferred into a green house. 24 days after inoculation, the degree of infection on the seedlings was examined.

The examination was made by dividing the leaves into the following four groups: healthy, slightly infected, infected to a medium degree, and badly infected, and the degree of infection was calculated basing on the following formula:

$$\text{Degree of infection} = \frac{\text{nr. of slightly infected leaves} \times 1 + \text{nr. of medium-infected leaves} \times 2 + \text{nr. of badly infected leaves} \times 3}{\text{total number of leaves examined} \times 3} \times 100$$

The test results are shown in Table 5.

Table 5

| Compounds tested | Concentration (ppm) | Ratio of infection leaves (%) | Degree of infection | Phytotoxicity |
|---|---|---|---|---|
| Compound B-1 | 1000 | 12.3 | 6.5 | — |
|  | 500 | 23.8 | 13.5 | — |
| Compound B-2 | 1000 | 12.0 | 8.0 | — |
|  | 500 | 25.1 | 14.1 | — |
| Compound B-3 | 1000 | 13.0 | 8.5 | — |
|  | 500 | 22.9 | 14.5 | — |
| Compound B-4 | 1000 | 14.2 | 9.6 | — |
|  | 500 | 26.7 | 15.9 | — |
| Compound B-5 | 1000 | 18.1 | 10.2 | — |
|  | 500 | 23.6 | 15.6 | — |
| Compound A | 1000 | 11.8 | 6.3 | — |
|  | 500 | 26.6 | 12.8 | — |
| Compound B-1 + Compound A | 500 + 500 | 1.2 | 0.2 | — |
| Compound B-2 + Compound A | 500 + 500 | 3.2 | 0.6 | — |
| Compound B-3 + Compound A | 500 + 500 | 1.5 | 0.3 | — |
| Compound B-4 + Compound A | 500 + 500 | 3.5 | 1.2 | — |
| Compound B-5 + Compound A | 500 + 500 | 2.4 | 1.1 | — |
| *Difoltan (comparative compound) | 800 | 11.5 | 8.4 | — |
| Non-treated | — | 100 | 96.5 | — |

*: N-(1,1,2,2-tetrachloroethylthio)cyclohexene-1,2-dicarboxyimide.

TEST EXAMPLE 6

Preventive effect on apple mildew

Apples (white winter pearmains) were cultured in 30 cm-diameter unglazed pots, and at a point where a slight degree of mildew has developed due to natural infection, the compositions of this invention prepared according to Example 5 were sprayed. After spray, natural infection was allowed to progress, and the degree of infection was examined three times at 10-days intervals. The test results are shown in Table 6. Degree of infection was calculated basing the formula of Test Example 5.

Table 6

| Compound tested | Concentration (ppm) | Degree of infection (%) Before spray | 10 days later | 20 days later | 30 days later | Phytotoxicity |
|---|---|---|---|---|---|---|
| Compound B-1 | 500 | 24.0 | 18.9 | 12.9 | 8.1 | — |
|  | 250 | 28.7 | 24.6 | 13.8 | 11.3 | — |
| Compound B-2 | 500 | 20.0 | 15.6 | 9.6 | 18.6 | — |
|  | 250 | 20.0 | 14.8 | 12.6 | 21.2 | — |
| Compound B-3 | 500 | 25.7 | 13.1 | 11.5 | 9.8 | — |
|  | 250 | 50.0 | 25.5 | 21.5 | 19.8 | — |
| Compound B-4 | 500 | 28.4 | 22.6 | 12.3 | 10.3 | — |
|  | 250 | 26.3 | 20.8 | 15.6 | 11.8 | — |
| Compound B-5 | 500 | 30.2 | 20.5 | 12.6 | 8.5 | — |
|  | 250 | 27.5 | 25.6 | 18.8 | 10.8 | — |
| Compound A | 500 | 28.2 | 16.5 | 11.2 | 4.4 | — |
|  | 250 | 26.5 | 21.3 | 15.6 | 10.4 | — |
| Compound B-1 + Compound A | 250 + 250 | 23.6 | 2.4 | 0 | 0 | |
| Compound B-2 + Compound A | 250 + 250 | 27.5 | 3.8 | 0.8 | 0 | |
| Compound B-3 + Compound A | 250 + 250 | 30.3 | 3.0 | 1.6 | 0 | |

Table 6-continued

| Compound tested | Concentration (ppm) | Degree of infection (%) | | | | Phytotoxicity |
|---|---|---|---|---|---|---|
| | | Before spray | 10 days later | 20 days later | 30 days later | |
| Compound B-4 + Compound A | 250 + 250 | 32.4 | 3.5 | 1.2 | 0 | |
| Compound B-5 + Compound A | 250 + 250 | 28.6 | 2.8 | 0.6 | 0 | |
| Non-sprayed | — | 16.7 | 24.0 | 35.4 | 42.8 | |

What is claimed is:

1. A fungicidal composition for agricultural and horticultural use comprising a suitable carrier and a fungicidally effective amount of a mixture consisting essentially of about 0.5 to 2 parts by weight of N-(4-fluorophenyl)-2,3-dichloromaleimide per part of at least one compound selected from the group consisting of a compound expressed by the formula:

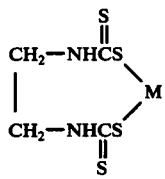

(where M represents manganese or zinc, and when M is manganese, zinc may coordinate in the molecules), N-trichloromethylthio-4-cyclohexene-1,2-dicarboxyimide and 8-oxyquinoline copper.

2. The composition of claim 1 comprising N-trichloromethylthio-4-cyclohexene-1,2-dicarboxyimide.

3. The composition of claim 1 comprising 8-oxyquinoline copper.

4. The composition of claim 1 comprising manganese ethylenebisdithiocarbamate.

5. The composition of claim 1 comprising zinc ethylenebisdithiocarbamate.

6. The composition of claim 1 comprising zinc ion coordinated manganese ethylenbisdithiocarbamate.

7. The composition of claim 1 containing about 1 to 2 parts of N-(4-fluorophenyl)-2,3-dichloromaleimide.

UNITED STATES PATENT AND TRADEMARK OFFICE
CERTIFICATE OF CORRECTION

PATENT NO. : 4,066,760
DATED : January 3, 1978
INVENTOR(S) : SEIGO KAWADA ET AL

It is certified that error appears in the above-identified patent and that said Letters Patent are hereby corrected as shown below:

Column 1, line 10, delete "fluro", and insert --fluoro--;

Column 1, line 41, delete "applies", and insert --apples--;

Column 1, line 64, delete "that", and insert --than--;

Column 6, line 14, delete "insectisides", and insert --insecticides--;

Column 6, line 15, after "0,0-dimethyl", insert -- - --;

Column 7, line 43, delete "powder", and insert --powders--;

Column 7, line 59, delete "lesion", and insert --lesions--;

Column 8, line 40, delete "powder", and insert --powders--;

Column 9, line 28, delete "were", and insert --was--;

Column 10, line 46, delete "basing", and insert --based on--.

Signed and Sealed this

Nineteenth Day of September 1978

[SEAL]

Attest:

RUTH C. MASON
*Attesting Officer*

DONALD W. BANNER
*Commissioner of Patents and Trademarks*